(12) United States Patent
McCord

(10) Patent No.: US 8,765,794 B2
(45) Date of Patent: *Jul. 1, 2014

(54) COMPOSITIONS AND METHODS FOR WOUND CARE

(76) Inventor: Darlene McCord, Coralville, IA (US)

(*) Notice: Subject to any disclaimer, the term of this patent is extended or adjusted under 35 U.S.C. 154(b) by 166 days.

This patent is subject to a terminal disclaimer.

(21) Appl. No.: 12/823,567

(22) Filed: Jun. 25, 2010

(65) Prior Publication Data
US 2010/0331377 A1 Dec. 30, 2010

Related U.S. Application Data

(60) Provisional application No. 61/220,485, filed on Jun. 25, 2009.

(51) Int. Cl.
*A61K 31/44* (2006.01)
*A61K 31/05* (2006.01)
*A61K 31/195* (2006.01)

(52) U.S. Cl.
USPC ........... 514/355; 514/731; 514/561; 514/277; 514/423

(58) Field of Classification Search
CPC ........... A61K 2300/00; A61K 31/4415; A61K 31/455
USPC .......................... 514/355, 731, 561, 277, 423
See application file for complete search history.

(56) References Cited

U.S. PATENT DOCUMENTS

| | | | |
|---|---|---|---|
| 5,733,535 A | 3/1998 | Hollingshead et al. | |
| 6,117,844 A | 9/2000 | Fredrickson | |
| 6,165,475 A | 12/2000 | Crea et al. | |
| 6,166,084 A * | 12/2000 | Bloor | 514/613 |
| 6,197,308 B1 | 3/2001 | Crea et al. | |
| 6,309,652 B1 | 10/2001 | Aeschbach et al. | |
| 6,358,542 B2 | 3/2002 | Cuomo et al. | |
| 6,416,808 B1 | 7/2002 | Crea | |
| 6,437,004 B1 * | 8/2002 | Perricone | 514/738 |
| 6,746,706 B1 | 6/2004 | van der Boom et al. | |
| 8,216,599 B2 | 7/2012 | Crea | |
| 2003/0086986 A1 * | 5/2003 | Bruijn et al. | 424/729 |
| 2003/0198687 A1 * | 10/2003 | Bennett et al. | 424/532 |
| 2003/0229141 A1 | 12/2003 | Yu et al. | |
| 2004/0097428 A1 * | 5/2004 | Hamdi et al. | 514/25 |
| 2004/0101507 A1 | 5/2004 | Predovan | |
| 2006/0045896 A1 * | 3/2006 | Morariu | 424/401 |
| 2006/0120980 A1 | 6/2006 | Eberl | |
| 2006/0121133 A1 | 6/2006 | Chomczynski | |
| 2006/0257351 A1 | 11/2006 | Chiba | |
| 2007/0065396 A1 | 3/2007 | Morariu | |
| 2007/0207228 A1 | 9/2007 | Giuliani et al. | |
| 2010/0113611 A1 | 5/2010 | Raederstorff et al. | |
| 2013/0005682 A1 | 1/2013 | Raederstorff et al. | |

FOREIGN PATENT DOCUMENTS

| | | |
|---|---|---|
| EP | 0123637 A1 | 10/1984 |
| EP | 2070545 A1 | 6/2009 |
| JP | 08119825 * | 10/1994 |
| JP | 08119825 * | 5/1996 |
| JP | 2007119431 A | 5/2007 |
| WO | WO0036936 A2 | 6/2000 |
| WO | WO2004/032873 A2 | 4/2004 |
| WO | WO2006/020588 A1 | 2/2006 |
| WO | WO2008/006581 A2 | 1/2008 |
| WO | WO2008128629 A1 | 10/2008 |

OTHER PUBLICATIONS

Fleck (Advances in Skin and Wound Care: The Journal for Prevention and Healing Jun. (2007) pp. 315-321 (numbered as 1-13).*
(English Translation), Oct. 1994, Japan, Ando.*
Snell (J. Anat. Lond. (1963), 97, 2; 243-253).*
Fleck (Advances in Skin and Wound Care: The Journal for Prevention and Healing Jun. 2007 pp. 315-321.*
Edwards Symposium on Advanced Wound Care 2005, 2 pages).*
Taavoni, S., et al., Effects of olive oil on striae gravidarum in the second trimester of pregnancy, Complementary Therapies in Clinical Practice, 2011, 167-169, 17.
Kranke, B., et al., Olive oil-contact sensitizer or irritant?, Contact Dermatitis, 1997, 5-10, 36.
International Search Report issued on PCT/US2010/040008 mailed Apr. 1, 2011.
Gupta, V. J., Third party submission to United States Patent and Trademark Office on Feb. 9, 2011, 19 pages.
Hengartner, M. O., The biochemistry of apoptosis, Nature, 2000, 770-776, 407.
PCT Search Report for PCT/US2010/045049, dated Jan. 28, 2011.
Angelo, S. D., et al., Hydroxytyrosol, a natural antioxidant from olive oil, prevents protein damage induced by long-wave ultraviolet radiation in melanoma cells, Free Radical Biology & Medicine, 2005, 908-919, 38.
Fabiani, R., et al., Cancer chemoprevention by hydroxytyrosol isolated from virgin olive oil through G1 cell cycle arrest and apoptosis, European Journal of Cancer Prevention, 2002, 351-358, 11.
Ragione, F. D., et al., Hydroxytyrosol, a Natural Molecule Occurring in Olive Oil, Induces Cytochrome c-Dependent Apoptosis, Biochemical and Biophysical Research Communications, 2000, 733-739, 278.
Deiana, M., et al., Protective effect of hydroxytyrosol and its metabolite homovanillic alcohol on H2O2 induced lipid peroxidation in renal tubular epithelial cells, Food and Chemical Toxicology, 2008, 2984-2990, 46.
Fabiani, R., et al., Inhibition of Cell Cycle Progression by Hydroxytyrosol is Associated with Upregulation of Cyclin-Dependent Protein Kinase Inhibitors p21AWAF1/Cip1 and p27AKip1 and with Induction of Differentiation in HL60 Cells, The Journal of Nutrition: Nutrition and Disease, 2008, 42-48.

(Continued)

*Primary Examiner* — Shirley V Gembeh
(74) *Attorney, Agent, or Firm* — McKee, Voorhees & Sease, P.L.C.

(57) ABSTRACT

The present disclosure relates to compositions for and methods of repairing the stratum corneum, compositions and methods for inhibiting excessive transepidermal water loss, compositions for and methods of treating skin that is distressed or wounded as a result of a disease or other biological condition or process (as distinguished from wounds resulting from trauma), compositions for and methods of treating chronic wounds, and compositions for the inhibition and treatment of necrosis and extended quiescence that result in cellular necrosis instead of normal proliferation.

39 Claims, No Drawings

(56) References Cited

OTHER PUBLICATIONS

Guichard, C., et al., Dihydroxyphenylethanol induces apoptosis by activating serine/threonine protein phosphatase PP2A and promotes the endoplasmic reticulum stress response in human colon carcinoma cells, Carcinogenesis, 2006, 1812-1827, 27(9).

Liu, Z., et al., Hydroxytyrosol protects retinal pigment epithelial cells from acrolein-induced oxidative stress and mitochondrial dysfunction, Journal of Neurochemistry, 2007, 2690-2700, 103.

Manna, C., et al., Protective Effect of the Phenolic Fraction from Virgin Olive Oils against Oxidative Stress in Human Cells, Journal of Agricultural and Food Chemistry, 2002, 6521-6526, 50.

Dog, T. L., Menopause: a review of botanical dietary supplements, The American Journal of Medicine, 2005, 98S-108S, 118(12B).

Johnson, B. M., In Vitro Formation of Quinoid Metabolites of the Dietary Supplement *Cimicifuga racemosa* (Black Cohosh), Chemical Research in Toxicology, 2003, 838-846, 16(7).

Fernandez-Bolanos et al., Potential use of olive by-products Extraction of interesting organic compounds from olive oil waste, Grasas y Aceites, 2006, 95-106, 57(1).

Cosenza, S. C., et al. Evidence That the Time of Entry into S is Determined by Events Occurring in Early G1, The Journal of Biological Chemistry, 1988, 12751-12758, 263(25).

Coller, H. A., A New Description of Cellular Quiescence, PLos Biology, 2006, 329-349, 4.

Gray, J. V., et al., "Sleeping Beauty": in *Saccharomyces cerevisiae*, Microbiology and Molecular Biology Reviews, 2004, 187-206, 68(2).

Abu Ali Ibn-e-Sina; Al-Qaanoon-fil-Tibb, vol. II (lith century AD), Institute of History of Medicine and Medical Research, Jamia Hamdard, New Delhi-62, 1987 AD p. 213-215; pertinent portion of the listed publications and the English language translation, including the terminology conversion from the contents of Traditional Knowledge Digital Library provided by V. K. Gupta in Third Party Submission filed Feb. 9, 2011.

Abu Bakr Mohammad.Bin Zakariyya Al-Razi; Kitaab-al-Haawi-fil-Tibb,vol. ill (9th century AD), Dayerah-al-Ma'aarif Usmania, Hyderabad, (Second Edition) 1977 AD p. 321; pertinent portion of the listed publications and the English language translation, including the terminology conversion from the contents of Traditional Knowledge Digital Library provided by V. K. Gupta in Third Party Submission filed Feb. 9, 2011.

Abu Bakr Mohammad.Bin Zakariyya Al-Razi; Kitaab-al-Haawi-fil-Tibb, vol. XX (9th century AD), Dayerah-al-Ma'aarifUsmania, Hyderabad, (First Edition) 1967 AD p. 558; pertinent portion of the listed publications and the English language translation, including the terminology conversion from the contents of Traditional Knowledge Digital Library provided by V. K. Gupta in Third Party Submission filed Feb. 9, 2011.

Mohammad Azam Khan; Ikseer Azam, vol. IV (19th century AD), Matba Nizami, Kanpur, 1872 AD p. 283; pertinent portion of the listed publications and the English language translation, including the terminology conversion from the contents of Traditional Knowledge Digital Library provided by V. K. Gupta in Third Party Submission filed Feb. 9, 2011.

Ziya Al- Din Abdullah Ibn Al- Baitar; Al-Jaam'e-li-Mufradaat-al-Advia-wal-Aghzia,vol. IV (13th century AD), Matba Amra, Cairo, Egypt, 1874 AD p. 105; pertinent portion of the listed publications and the English language translation, including the terminology conversion from the contents of Traditional Knowledge Digital Library provided by V. K. Gupta in Third Party Submission filed Feb. 9, 2011.

Abu Bakr Mohammad,Bin ZakariyyaAl-Razi; Kitaab-al-Haawi-fil-Tibb, Vol.XX(9th century AD), Dayerah-al- Ma'aarif Usmania, Hyderabad, (First Edition) 1967 AD p. 180; pertinent portion of the listed publications and the English language translation, including the terminology conversion from the contents of Traditional Knowledge Digital Library provided by V. K. Gupta in Third Party Submission filed Feb. 9, 2011.

Scalbert, Augustin, et al., "Absorption and metabolism of polyphenols in the gut and impact on health", Biomed Pharmacother 56 (2002), 276-282.

Visioli, Fancesco, et al., "Antioxidant and Other Biological Activities of Olive Mill Waste Waters", J. Agric. Food Chem. 1999, 47, 3397-3401.

Haloui, Ehsen, et al., "Hydroxytyrosol and oleuropein from olive leaves: Potent anti-inflammatory and analgesic activities", Journal of Food, Agriculture & Environment, vol. 9 (3 & 4) (2011), 128-133.

Granados-Principal, Sergio, et al., "Hydroxytyrosol: from laboratory investigations to future clinical trials", Nutrition Reviews vol. 68 (4), 2010: 191-206.

Zhu, Lu, et al., "Hydroxytyrosol protects against oxidative damage by simultaneous activation of mitochondrial biogenesis and phase II detoxifying enzyme systems in retinal pigment epithelial cells", Journal of Nutritional Biochemistry (2010), pp. 1-10.

Zanichelli, Dario, et al., "Inhibition of *Staphylococcus aureus* by Oleuropein Is Mediated by Hydrogen Peroxide", Journal of Food Protections, vol. 68, No. 7, 2005, pp. 1492-1496.

Washington, Jennifer M., et al., "L-Proline induces differentiation of ES cells: a novel role for an amino acid in the regulation of pluripotent cells in culture", Am J Physiol Cell Physiol 298 (2010), C982-C992.

Tuck, Kellie L., et al., "Major phenolic compounds in olive oil: metabolism and health effects", Journal of Nutritional Biochemistry 13 (2002), 636-644.

Sarsour, Ehab H., et al., "Manganese Superoxide Dismutase Regulates a Metabolic Switch during the Mammalian Cell Cycle", 2012, pp. OF1-OF10.

Sarsour, Ehab H., et al., "MnSOD activity regulates hydroxytyrosol-induced extension of chronological lifespan", American Aging Association 2011, pp. 1-15.

Haber, C. Andrew, et al., "N-acetylcysteine and taurine prevent hyperglycemia-induced insulin resistance in vivo: possible role of oxidative stress", Am J Physiol Endocrinol Metab 285 (2003), E744-E753.

Victor, Victor M., et al., "N-acetylcysteine Protects Mice from Lethal Endotoxemia by Regulating the Redox State of Immune Cells", Free Radical Research, vol. 37 No. 9 (Sep. 2003), pp. 919-929.

Gonzalez-Correa, Jose Antonia, et al., "Neuroprotective effect of hydroxytyrosol and hydroxytyrosol acetate in rat brain slices subjected to hypoxia-reoxygenation", Neuroscience Letters 446 (2008), 143-146.

Vissers, Maud N., et al., "Olive Oil Phenols Are Absorbed in Humans", American Society for Nutritional Sciences, 2002, pp. 409-417.

Bisignano, Giuseppe, et al., "On the In-vitro Antimicrobial Activity of Leuropein and Hydroxytyrosol", J. Pharm. Pharmacol. 1999, 51: 971-974.

Webb, K.E., et al., "Peptide absorption: a review of current concepts and future perspectives", J Anim Sci 1992, 70: 3248-2357.

Pereira, Ana Paula, et al., "Phenolic Compounds and Antimicrobial Activity of Olive (*Olea europaea* L. Cv. Cobrancosa) Leaves", Molecules 2007, 12, 1153-1162.

Romani, Annalisa, et al., "Polyphenolic Content in Five Tuscany Cultivars of Olea europaea L.", J. Agric. Food Chem. 1999, 47, 964-967.

Walter, W.M., Jr., et al., "Preparation of Antimicrobial Compounds by Hydrolysis of Oleuropein from Green Olives", Applied Microbiology, Nov. 1973, vol. 26, No. 5, p. 773-776.

Capasso, Renato, et al., "Production of Glucose and Bioactive Aglycone by Chemical and Enymatic Hydrolysis of Purified Oleuropein from Olea Europea", Applied Biochemistry and Biotechnology, vol. 61, 1996, pp. 365-377.

Matthews, D.M., et al., "Protein absorption", J. clin. Path., 24, Suppl. (Roy. Coll. Path.), 5, 2012, pp. 29-40.

EP0123637, Soto Lucien—English Abstract.

JP2007119431, Ichimaru Pharcos—English Abstract.

McCord, Darlene, PCT/US2010/045049 filed Jan. 12, 2012, "The Extended European Search Report", dated Mar. 19, 2013.

* cited by examiner

COMPOSITIONS AND METHODS FOR WOUND CARE

CROSS-REFERENCE TO RELATED APPLICATIONS

This application claims priority to U.S. Ser. No. 61/220,485, filed Jun. 25, 2009, entitled COMPOSITIONS AND METHODS FOR WOUND CARE, the contents of which is hereby incorporated by reference in their entirety.

FIELD OF THE INVENTION

The present invention generally relates to topical compositions and methods for reversing damage to skin cells and, in particular, to compositions and methods for wound healing and inhibiting necrosis. The compositions and methods may be used, for example, in the treatment of skin that is distressed or wounded as result of a disease or other biological condition or process.

BACKGROUND OF THE INVENTION

The epidermis is the outermost layer of the skin and forms the protective wrap over the body's surface. The epidermis can be further subdivided into strata with the outermost layer of the epidermis being the stratum corneum which is responsible for keeping water in the body and keeping harmful chemicals and pathogens out, making skin a natural barrier to infection. Transepidermal water loss, i.e., water that passes from inside a body (animal or plant) through the epidermal layer (skin) to the surrounding atmosphere via diffusion and evaporation processes, is a normal part of the cellular activity and regulated by the stratum corneum. Excessive transepidermal water loss, however, activates an inflammatory response in the epidermis and the dermis.

Corneotherapy is a skin care concept based on repairing the stratum corneum and therefore improving the function of the skin barrier. Topically applied substances influence the biochemistry in the horny layer of the skin and subsequent processes in deeper skin layers, which consequently have effects on the constitution of the horny layer, creating a cyclical effect that starts at the surface of the skin. A healthy and functioning skin barrier provides overall protection against dehydration and the penetration of germs, allergens, irritants, radicals, and radiation. This protection supports a gradual reduction in inflammation and other skin problems as the external causative agents are repelled by an intact skin barrier.

Wound healing, or wound repair, is a process in which the skin repairs itself after injury. In normal skin, the epidermis (outermost layer) and dermis (inner or deeper layer) exists in a steady-stated equilibrium, forming a protective barrier against the external environment. Once the protective barrier is broken, the normal (physiologic) process of wound healing is immediately set in motion.

The wound healing process is susceptible to interruption or failure leading to the formation of chronic non-healing wounds, that is, a wound that does not heal in an orderly manner and in a predictable amount of time as compared to wounds resulting from surgery (also sometimes known as wounds of primary intention) or wounds caused by trauma; for example, wounds that do not heal within several months are often considered chronic. Chronic wounds present a particularly difficult problem to treat and are typically classified into three categories: venous ulcers, diabetic, and pressure ulcers. A small number of wounds that do not fall into these categories may be due to causes such as radiation poisoning or ischemia. Chronic wounds, especially ulcerative wounds such as pressure ulcers (bed sores), diabetic ulcers, venous ulcers, etc. that, without treatment, are often trapped in the inflammation phase of wound healing. These types of wounds often accelerate quickly and damage not only the skin, but underlying tissues as well. The excessive healing time required for these types of wounds can lead to secondary complications, such as permanent underlying tissue damage, nerve damage, loss of circulation, and even mortality.

Pressure ulcers and certain other chronic wounds are sometimes categorized according to severity by the use of stages. According to one protocol, Stage I is characterized by a surface reddening of the skin; to the unaided eye, the skin is unbroken and the wound is superficial. Stage II is characterized by a partial thickness skin loss involving the dermis and/or epidermis, typically presenting as an abrasion, blister (broken or unbroken), shallow crater or other lesion, that is visible to the unaided eye. Stage III wounds extend through all of the layers of the skin and are a primary site for a serious infection to occur. Stage IV wounds extend through the skin and involves underlying muscle, tendons and bone. The term "peripheral to the wound" or "peri-wound area" refers to the area adjacent to a wound (a Stage II, III or IV wound) and typically extends from immediately adjacent the wound up to about 3 to 5 cm.

There are two distinct mechanisms for cell death. Apoptosis is the result of "normal" or programmed cell death. Through this physiological process cells are routinely eliminated, giving balance to the proliferation of new cells. During apoptosis the outer membrane of the cell forms "bubbles" known as blebs. The content of the cells becomes incased in the blebs. The blebs separate from the cell and are digested by nearby cells or macrophages. This orderly process greatly reduces toxicity to surrounding cells.

Necrosis is the other form of cell death. This is not a programmed event and is known as "accidental" death. This pathological process occurs when cells are exposed to extreme stress, chemical insult, and resultant free radical damage. The early stages of necrosis involve a swelling of the cell called oncosis. During oncosis the cell and its organelles begin to swell due to an exchange in the cell's potassium to sodium ratios. Necrosis, after the oncosis stage, is an explosive event where the cells contents stream directly into the surrounding cells environment causing damage and an immune response. Controlling necrosis during the early oncosis stage is important. Up to this point, necrosis is a reversible event. The morphology of cells dying by necrosis centers on changes in the cell's permeability. Hengartner M O, The biochemistry of apoptosis. *Nature* 407:770-776, 2000. Osmotic changes take place during an exchange of cytosol potassium and extracellular sodium. Early stage necrosis, known as oncosis, is characterized by the dilation or swelling of the cell and its organelles due to this exchange. Cell survival of this non-programmed event is dependent upon repairing the cell's membrane and stopping the flow of sodium ions into the cells interior. Repair of the cell's membrane and improvement in the cell's environment to more homeostatic conditions are paramount to survival.

Quiescence is the counterpart to proliferation and is a normal part of the cell cycle. The cell's replicative cycle involves a myriad of molecular events that occur during the quiescent state ($G_0$) and trigger the progression to the prereplicative ($G_1$) phase. Cosenza S C, Owen T A, Soprano D R, Soprano K J, Evidence That the Time of Entry into S is Determined by Events Occurring in Early $G_1$. *J Biological Chem.* 263; 12751-12758; 1988. The $G_0$ phase represents not just the absence of signals for mitosis but an active repression of the genes needed for mitosis. This is an important distinction since cancer cells cannot enter $G_0$ and as a consequence become immortal.

During quiescence, a cell will reduce in size yet remain dynamic and metabolically active. A quiescent cell is more notable for what it doesn't do such as synthesize DNA. Coller H A, Sang L, Roberts J M, A New Description of Cellular Quiescence. *PLos Biology* 4:0329-0349 2006. Quiescent cells are in a "state-of-readiness," like hibernation, waiting for the appropriate signal that it is once more time to move to the $G_1$ phase. Cells have a built-in conservation mechanism allowing it to survive for extended periods. Gray J V, Petsko G A, Johnston C, Ringe D, Singer R A, Werner-Washburne M, "Sleeping Beauty": in *Saccharomyces cerevisiae, Microbiology and Molecular Biology Reviews* 68:2; 187-206, 2004. If the cell remains in the quiescence state for an extended period, however, its ability to proliferate diminishes. Stated differently, the longer a cell stays in abnormal quiescence the more likely it becomes that the cell will die via necrosis. Just as with early stage necrosis, however, early quiescence is a reversible event that can be corrected by changing the cell's environment and reduction of free radicals in the cell's environment appears to be critical to the reversal process. See, e.g., Coller H A, Sang L, Roberts J M, A New Description of Cellular Quiescence PLoS Biol 4(3):e83.doi:10.1371/journal.pbio.0040083 (2006).

SUMMARY OF THE INVENTION

Among the various aspects of the present invention may be noted topical compositions for and methods of repairing the stratum corneum, compositions and methods for inhibiting excessive transepidermal water loss, topical compositions for and methods of treating skin that is distressed or wounded as a result of a disease or other biological condition or process (as distinguished from wounds resulting from trauma), topical compositions for and methods of treating chronic wounds, and topical compositions for the inhibition and treatment of necrosis and extended quiescence that result in cellular necrosis instead of normal proliferation.

Briefly, therefore, the present invention is directed to a process for treating an open skin wound, the open skin wound being surrounded by a peri-wound region. The process comprises topically applying an aqueous composition to the peri-wound region, the aqueous composition comprising about 5 to about 250 μM hydroxytyrosol. In one embodiment, an aqueous composition containing hydroxytyrosol in a concentration not in excess of about 15 μM hydroxytyrosol is also applied to the open wound.

Another aspect of the invention is a process for inhibiting excessive transepidermal water loss through the stratum corneum. The process comprises topically applying an aqueous composition to the stratum corneum, the aqueous composition comprising about 5 to about 250 μM hydroxytyrosol.

Another aspect of the present invention is a process for treating skin that is distressed or wounded as a result of a disease or other metabolic condition. The process comprises topically applying an aqueous composition to the skin, the aqueous composition comprising about 5 to about 250 μM hydroxytyrosol.

Another aspect of the present invention is a composition for topical application for wound care, the composition comprising a pharmaceutically acceptable carrier and about 10 to about 250 μM hydroxytyrosol. In one embodiment the composition additionally comprises N-acetyl cysteine.

Another aspect of the present invention is a composition for topical application for wound care, the composition comprising a pharmaceutically acceptable carrier and up to about 15 μM hydroxytyrosol. In one embodiment the composition additionally comprises N-acetyl cysteine.

Other objects and features will be in part apparent and in part pointed out hereinafter.

DETAILED DESCRIPTION OF THE INVENTION

Surprisingly, it has been discovered that hydroxytyrosol, a potent anti-oxidant, can influence whether a cell is in a quiescent or proliferative state. More specifically, when present at a concentration above a threshold level, hydroxytyrosol can induce proliferative cells into a quiescent state and help maintain cells in a pre-existing quiescent state. Based upon evidence obtained to-date, the threshold concentration is about 10 μM hydroxytyrosol.

In addition, it has also been discovered that hydroxytyrosol, along with other optional components can improve the overall health of a cell and cell viability. In one embodiment, therefore, a composition containing hydroxytyrosol in a concentration of at least about 1 μM hydroxytyrosol is topically applied to a wound, peri-wound or other skin area. In another preferred embodiment, the composition comprises hydroxytyrosol and an additional component having a molecular weight not in excess of 500 Daltons that improves the health or viability of skin cells. In a preferred embodiment, the composition comprises hydroxytyrosol and N-acetyl cysteine. In yet another embodiment, the composition comprises hydroxytyrosol, N-acetyl cysteine and at least one additional component having a molecular weight not in excess of 500 Daltons that improves the health or viability of skin cells.

The compositions described herein are employed as topical compositions. They are preferably applied to the surface of the skin, mucosal cells and tissues (e.g., alveolar, buccal, lingual, masticatory, or nasal mucosa, and other tissues and cells that line hollow organs or body cavities) or exposed tissue.

Without being bound to any particular theory and based upon evidence obtained to-date, compositions of the present invention may be used to improve the health and viability of skin cells that are diseased or distressed as a result of a metabolic condition. For example, compositions comprising hydroxytyrosol may be used to reduce the concentration of free-radicals in the cells of skin tissue to improve cellular function. In addition, compositions comprising sufficient hydroxytyrosol may be used to induce cells into or maintain them in a reversible quiescent state to provide them with time to heal and return to a more viable state with a reduced risk of necrosis. In a preferred embodiment, such compositions comprise N-acetyl cysteine. In another preferred embodiment, such compositions additionally comprise N-acetyl cysteine. In another preferred embodiment, the composition comprises hydroxytyrosol, N-acetyl cysteine and an additional component having a molecular weight not in excess of 500 Daltons that improves the health or viability of skin cells. Such additional components, for example, may be selected from the group consisting of glycine, L-taurine, L-proline, niacinamide (vitamin B3), pyridoxine (vitamin B6), methylsulfonylmethane, and combinations thereof.

The compositions and methods of the present invention may be used to treat skin that is dry, cracked, scaly, or exhibiting redness or edema but otherwise appears intact to the unaided eye. These symptoms may be presented as a result of an underlying disease or metabolic condition such as diabetes or, alternatively, may be caused by excessive transepidermal water loss. Transepidermal water loss in excess of about 5 g/hr/cm$^2$ can activate an inflammatory response in the epidermis and dermis. Many factors, such as relative humidity below 40%, changes in skin pH, normal aging and disruption of the stratum corneum contribute to excessive transepidermal water loss.

The compositions and methods of the present invention may be used to treat more serious wounds, that is, wounds characterized by a partial or total thickness skin loss, including wounds that are at risk of necrosis. When a wound is characterized by a partial or total thickness skin loss, one of the phases of wound healing is the proliferative phase. The proliferative phase typically includes angiogenesis, collagen deposition, granulation tissue formation, epithelialization, and wound contraction. Wound closure thus requires that cells be in a proliferative phase and it is preferred, therefore, that any composition applied to an open wound not induce the cells in the open wound area into a quiescent state.

In general, it is preferred that compositions applied to an open wound contain hydroxytyrosol in a concentration that is less than the threshold concentration at which quiescence is induced or maintained. Stated differently, it is generally preferred that compositions applied to Stage II, Stage III or Stage IV wounds contain hydroxytyrosol in a concentration that is less than the threshold concentration at which quiescence is induced or maintained. In one embodiment, therefore, compositions applied to an open or Stage II, III or IV wound contain hydroxytyrosol in a concentration not in excess of about 15 µM hydroxytyrosol. For example, compositions applied to an open or Stage II, III or IV wound may contain hydroxytyrosol in a concentration of at least about 1 µM but not in excess of about 15 µM hydroxytyrosol. By way of further example, such compositions may contain hydroxytyrosol in a concentration of about 1 to about 12 µM. In certain embodiments, the concentration of hydroxytyrosol in such compositions will typically be between about 1 µM and 10 µM hydroxytyrosol.

In other regions, that is, regions appearing intact to the unaided eye such as (i) the peri-wound region surrounding an open wound, (ii) skin that is dry, cracked, scaly, or exhibiting redness or edema but otherwise appears intact to the unaided eye, or (iii) skin experiencing excessive transepidermal water loss but otherwise appears intact to the unaided eye may be treated with compositions containing hydroxytyrosol in a concentration that is greater than the concentration at which quiescence is induced or maintained. Stated differently, it is generally preferred that compositions applied to wounds not characterized by a partial or total thickness skin loss (Stage I or less severe wounds sometimes called Stage 0) contain hydroxytyrosol in a concentration that is greater than the threshold concentration at which quiescence is induced or maintained. In one embodiment, therefore, compositions applied to a Stage 0 or Stage I wound contain hydroxytyrosol in a concentration in excess of 5 µM but not in excess of about 250 µM hydroxytyrosol. For example, compositions applied to (i) the peri-wound region surrounding an open wound, (ii) skin that is dry, cracked, scaly, or exhibiting redness or edema but otherwise appears intact to the unaided eye, or (iii) skin experiencing excessive transepidermal water loss but otherwise appears intact to the unaided eye may contain hydroxytyrosol in a concentration in excess of about 250 µM. In one embodiment, such compositions may contain hydroxytyrosol in a concentration of about 5 µM to about 250 µM. In certain embodiments, such compositions may contain hydroxytyrosol in a concentration of about 7 µM to about 225 µM. In certain embodiments, such compositions may contain hydroxytyrosol in a concentration of about 10 µM to about 200 µM. In certain embodiments, such compositions may contain hydroxytyrosol in a concentration of at least 15 µM but not in excess of 200 µM.

Treatment of a Stage II, III or IV wound preferably comprises treatment of the peri-wound region with a first composition and treatment of the wound region with a second composition wherein the first composition contains hydroxytyrosol in a concentration at which quiescence is induced or maintained and the second composition contains hydroxytyrosol in a concentration that is less than the concentration at which quiescence is induced or maintained. Typically, the two compositions will be applied 2 to 3 times daily at regularly spaced intervals until the wound has filled (i.e., closes); at that point, the first composition may be applied 2 to 3 times daily at regularly spaced intervals to the closed wound and the peri-wound region. Advantageously, application of the first composition to the closed wound will tend to reduce scarring. In one embodiment, the first composition will be applied to the closed wound for up to 18 months after closure of the wound without a recurrence of the wound.

Treatment of regions appearing intact to the unaided eye such as (i) the peri-wound region surrounding an open wound, (ii) skin that is dry, cracked, scaly, or exhibiting redness or edema but otherwise appearing intact to the unaided eye, or (iii) skin experiencing excessive transepidermal water loss but otherwise appearing intact to the unaided eye may be treated with compositions containing hydroxytyrosol in a concentration that is greater than the concentration at which quiescence is induced or maintained until the region is asymptomatic. For peri-wounds, the composition is preferably applied to the entire peri-wound region and adjacent skin within at least about 1 cm of the peri-wound region. Typically, the composition will be applied 2 to 3 times daily at regularly spaced intervals at least until the region is asymptomatic.

Compositions containing hydroxytyrosol in a concentration that is greater than the concentration at which quiescence is induced or maintained may also be applied prophylactically to regions that are perceived to be at risk of a chronic wound, such as venous ulcers and diabetic ulcers. In one embodiment, chronic wounds are treated using a composition of the present invention to help reverse the damage to the cells in the wound and peri-wound areas and inhibit necrosis. For example, such compositions may be applied to regions in which there are symptoms of neuropathy or lack of capillary integrity. By way of further example, such compositions may be applied to the lower leg, e.g., from the knee to the tips of the toes.

In addition to hydroxytyrosol, the topical compositions of the present invention may contain N-acetyl cysteine and/or an additional component having a molecular weight not in excess of 500 Daltons that improves the health or viability of skin cells. Such additional components, for example, may include other antioxidants, vitamins, minerals, and/or amino acids. Non-limiting examples of other antioxidants include ascorbic acid (vitamin C) and its salts, ascorbyl esters of fatty acids, ascorbic acid derivatives (e.g., magnesium ascorbyl phosphate, sodium ascorbyl phosphate, and ascorbyl sorbate), EGCG, oleuropein, tocopherol (vitamin E), tocopherol sorbate, tocopherol acetate, other esters of tocopherol, tyrosol, butylated hydroxy benzoic acids and their salts, gallic acid and its alkyl esters such as propyl gallate, uric acid and its salts and alkyl esters, sorbic acid and its salts, lipoic acid, amines (e.g., N,N-diethylhydroxylamine and amino-guanidine), sulfhydryl compounds (e.g., glutathione), dihydroxy fumaric acid and it salts, glycine pidolate, arginine pilolate, nordihydroguaiaretic acid, bioflavinoids, curcumin, lyseine, methionine, proline, superoxide dismutase, resveratrol, and other polyphenols. In another embodiment, the composition comprises hydroxytyrosol, N-acetyl cysteine, and one or more of cystine, cystine derivatives, vitamin C, tannic acid, vitamin E, vitamin E derivatives, catechin, niacin, unsaturated fatty acids, vitamin P, vitamin Q, glutathione, isoflavones, guava, selenium, oleuropein or other polyphenol(s). In one embodiment, the composition comprises hydroxytyrosol, N-acetyl cysteine and one or more of glycine, L-taurine, L-proline, niacinamide (vitamin B3), pyridoxine (vitamin B6), and methylsulfonylmethane.

In one embodiment, the composition contains non-amino acid additives such as aloe vera, oat extract, hyaluronic acid, betaglucan or like substance to provide glycosaminoglycans for extracellular matrix protection. Vitamins may be additives, especially vitamins A/D3, all B vitamins and all stable C vitamins. Omega 3 and 6 fatty acids will be balanced with the greater percentage being 3. In one embodiment, the composition may contain other antioxidants, anti-inflammatory agents and tissue repair ingredients known to have wound healing benefits. For example, in one embodiment, the composition contains olive leaf extract, vitamin A/D3, Vitamin C, and essential fatty acids from olive oil, canola oil, safflower oil, borrage oil and sunflower oil. Also preferably, olive leaf extract is present in the composition of the present invention.

In one embodiment, the composition contains N-acetyl cysteine and hydroxytyrosol and the weight ratio of N-acetyl cysteine to hydroxytyrosol to between 1:1 and 50:1, respectively. In one embodiment, the composition contains N-acetyl cysteine and hydroxytyrosol and the weight ratio of N-acetyl cysteine to hydroxytyrosol is between 10:1. and 30:1, respectively. For example, in one such embodiment, the composition contains N-acetyl cysteine and hydroxytyrosol and the weight ratio of N-acetyl cysteine to hydroxytyrosol is between 20:1 and 25:1, respectively.

In one embodiment, the composition contains glycine and hydroxytyrosol and the weight ratio of glycine to hydroxytyrosol to between 1:1 and 50:1, respectively. In one embodiment, the composition contains glycine and hydroxytyrosol and the weight ratio of glycine to hydroxytyrosol is between 30:1 and 40:1, respectively. For example, in one such embodiment, the composition contains glycine and hydroxytyrosol and the weight ratio of glycine to hydroxytyrosol is about 35:1, respectively.

In one embodiment, the composition contains L-taurine and hydroxytyrosol and the weight ratio of L-taurine to hydroxytyrosol to between 1:1 and 50:1, respectively. In one embodiment, the composition contains L-taurine and hydroxytyrosol and the weight ratio of L-taurine to hydroxytyrosol is between 20:1 and 50:1, respectively. In one embodiment, the composition contains L-taurine and hydroxytyrosol and the weight ratio of L-taurine to hydroxytyrosol is between 30:1 and 40:1, respectively. For example, in one such embodiment, the composition contains L-taurine and hydroxytyrosol and the weight ratio of L-taurine to hydroxytyrosol is about 35:1, respectively.

In one embodiment, the composition contains L-proline and hydroxytyrosol and the weight ratio of L-proline to hydroxytyrosol to between 1:1 and 20:1, respectively. In one embodiment, the composition contains L-proline and hydroxytyrosol and the weight ratio of L-proline to hydroxytyrosol is between 1:1 and 10:1, respectively. In one embodiment, the composition contains L-proline and hydroxytyrosol and the weight ratio of L-proline to hydroxytyrosol is between 1:1 and 5:1, respectively.

In one embodiment, the composition contains methylsulfonylmethane and hydroxytyrosol and the weight ratio of methylsulfonylmethane to hydroxytyrosol to between 1:1 and 30:1, respectively. In one embodiment, the composition contains methylsulfonylmethane and hydroxytyrosol and the weight ratio of methylsulfonylmethane to hydroxytyrosol is between 5:1 and 25:1, respectively. In one embodiment, the composition contains methylsulfonylmethane and hydroxytyrosol and the weight ratio of methylsulfonylmethane to hydroxytyrosol is between 10:1 and 20:1, respectively.

In one embodiment, the composition contains niacinamide and hydroxytyrosol and the weight ratio of niacinamide to hydroxytyrosol to between 1:1 and 10:1, respectively. In one embodiment, the composition contains niacinamide and hydroxytyrosol and the weight ratio of niacinamide to hydroxytyrosol is between 1:1 and 5:1, respectively. In one embodiment, the composition contains niacinamide and hydroxytyrosol and the weight ratio of niacinamide to hydroxytyrosol is between 1:1 and 2:1, respectively.

In one embodiment, the composition contains pyridoxine and hydroxytyrosol and the weight ratio of pyridoxine to hydroxytyrosol to between 1:1 and 10:1, respectively. In one embodiment, the composition contains pyridoxine and hydroxytyrosol and the weight ratio of pyridoxine to hydroxytyrosol is between 1:1 and 5:1, respectively. In one embodiment, the composition contains pyridoxine and hydroxytyrosol and the weight ratio of pyridoxine to hydroxytyrosol is between 1:1 and 2:1, respectively.

In one preferred embodiment, the composition of the present invention contains hydroxytyrosol, N-acetyl cysteine and optionally one or more of glycine, L-taurine, L-proline, niacinamide (B3), pyridoxine (B6), and methylsulfonylmethane. In one example of this embodiment, the weight ratio N-acetyl cysteine to hydroxytyrosol is between 1:1 and 50:1, respectively, the weight ratio glycine to hydroxytyrosol is between 1:1 and 50:1, respectively, the weight ratio of L-taurine to hydroxytyrosol is between 1:1 and 50:1, respectively, the weight ratio of L-proline to hydroxytyrosol is between 1:1 and 20:1, respectively, the weight ratio of niacinamide to hydroxytyrosol is between 1:1 and 10:1, respectively, the weight ratio of pyridoxine to hydroxytyrosol is between 1:1 and 10:1, and the weight ratio of methylsulfonylmethane to hydroxytyrosol is between 1:1 and 30:1. In another example of this embodiment, the weight ratio N-acetyl cysteine to hydroxytyrosol is between 10:1 and 30:1, respectively, the weight ratio glycine to hydroxytyrosol is between 30:1 and 40:1, respectively, the weight ratio of L-taurine to hydroxytyrosol is between 20:1 and 50:1, respectively, the weight ratio of L-proline to hydroxytyrosol is between 1:1 and 10:1, respectively, the weight ratio of niacinamide to hydroxytyrosol is between 1:1 and 5:1, respectively, the weight ratio of pyridoxine to hydroxytyrosol is between 1:1 and 5:1, and the weight ratio of methylsulfonylmethane to hydroxytyrosol is between 10:1 and 30:1. In another example of this embodiment, the weight ratio N-acetyl cysteine to hydroxytyrosol is between 20:1 and 25:1, respectively, the weight ratio glycine to hydroxytyrosol is between 30:1 and 40:1, respectively, the weight ratio of L-taurine to hydroxytyrosol is between 30:1 and 40:1, respectively, the weight ratio of L-proline to hydroxytyrosol is between 1:1 and 5:1, respectively, the weight ratio of niacinamide to hydroxytyrosol is between 1:1 and 2:1, respectively, the weight ratio of pyridoxine to hydroxytyrosol is between 1:1 and 2:1, and the weight ratio of methylsulfonylmethane to hydroxytyrosol is between 10:1 and 20:1.

In each of the aforementioned embodiments, the components of the composition of the present invention may optionally be present in the form of an ester or a physiologically/pharmaceutically acceptable salt. Exemplary esters include the mono-, di- and triesters of hydroxytyrosol with (un)saturated carbonic acids R—COOH, whereby R is an alkyl or alkenyl chain having 2 to 22 carbon atoms. Exemplary pharmaceutically acceptable salts refers to salts prepared from pharmaceutically acceptable non-toxic acids, including inorganic salts and organic salts. Suitable non-organic salts include inorganic and organic acids such as acetic, benzenesulfonic, benzoic, camphorsulfonic, citric, ethenesulfonic, fumaric, gluconic, glutamic, hydrobromic, hydrochloric, isethionic, lactic, malic, maleic, mandelic, methanesulfonic, mucic, nitric, pamoic, pantothenic, phosphoric, succinic, sulfuric, tartaric acid, p-toluenesulfonic and other pharmaceutically acceptable salts as provided in Stahl and Wermuth "Pharmaceutical Salts Properties, Selection, and Use", 1st Ed, Wiley-VCH, 374 (2002). Thus, for example, the term "hydroxytyrosol" also encompasses pharmaceutically acceptable salts thereof such as the sodium or potassium salts, or others of the aforementioned salts, or an ester thereof.

For use in the composition of the present invention, hydroxytyrosol may be derived from natural sources or prepared by chemical synthesis. For example, the hydroxytyrosol may be obtained as an extract of, or otherwise derived from, olive leaves, olive fruits and vegetation water of olive oil production. When obtained as an extract, for example, of olive leaves, the extract will contain hydroxytyrosol, tyrosol, oleuropein, and other polyphenols. In one preferred embodiment, the hydroxytyrosol is obtained as an olive leaf extract of *Olea europaea*.

The composition may be in any form suitable for application to the body surface, and may comprise, for example, a cream, lotion, solution, suspension, emulsion, gel, ointment, paste, or the like, and/or may be prepared so as to contain liposomes, micelles, and/or microspheres. In certain embodiments, it is preferred, although not essential, that water be present. Thus, such a formulation may be aqueous, i.e., contain water, or, alternatively, may be nonaqueous. Where the formulation is nonaqueous, it may be optionally used in combination with an occlusive overlayer so that moisture evaporating from the body surface is maintained within the formulation upon application to the body surface and thereafter. In one preferred embodiment, the formulation is aqueous.

The principal differences between the physical dose forms noted above (e.g., creams, lotions, gels, and aqueous liquids) are their physical appearance and viscosity (or thickness), which are governed primarily by the presence and amount of emulsifiers and viscosity adjusters; the main ingredients are, in many cases, common among these product forms. Moreover, a particular topical formulation may often be prepared in a variety of these forms. Ointments, creams and lotions are often similar to one another, differing mainly in their viscosity (creams are typically thicker and more viscous than lotions); both lotions and creams may be opaque, translucent or clear and often contain emulsifiers, solvents (including water and alcohol) and viscosity adjusting agents. Ointments, creams and lotions also may optionally contain moisturizers and emollients, as well as fragrances, dyes/colorants, preservatives and active ingredients. Gels may be prepared with a range of viscosities, from thick (high viscosity) to thin (low viscosity) and differ principally from lotions and creams in that gels are often (but not exclusively) clear rather than opaque. Like lotions and creams, gels often contain emulsifiers, solvents (including water and alcohol) and viscosity adjusters, and may also contain moisturizers and emollients, fragrances, dyes/colorants, preservatives and active ingredients. Aqueous liquids are thinner than creams, lotions or gels, and are generally transparent; liquids usually do not contain emulsifiers. Liquid topical products often contain other solvents in addition to water (including alcohol) and may also contain viscosity adjusters, moisturizers and emollients, fragrances, dyes/colorants/pigments, preservatives and active ingredients.

Ointments, as is well known in the art of pharmaceutical formulation, are semisolid preparations that are typically based on petrolatum or other petroleum derivatives. The specific ointment base to be used, as will be appreciated by those skilled in the art, is one that will provide for optimum drug delivery, and, preferably, will provide for other desired characteristics as well, e.g., emolliency or the like. As with other carriers or vehicles, an ointment base should be inert, stable, nonirritating and nonsensitizing. Ointment bases may be grouped in four classes: oleaginous bases; emulsifiable bases; emulsion bases; and water-soluble bases (see, e.g., Remington: The Science and Practice of Pharmacy, 19th Ed. (Easton, Pa.: Mack Publishing Co., 1995), pages 1399-1404). Oleaginous ointment bases include, for example, vegetable oils, fats obtained from animals, and semisolid hydrocarbons obtained from petroleum. Emulsifiable ointment bases, also known as absorbent ointment bases, typically contain little or no water and include, for example, hydroxystearin sulfate, anhydrous lanolin, and hydrophilic petrolatum. Emulsion ointment bases are generally either water-in-oil (W/O) emulsions or oil-in-water (O/W) emulsions, and include, for example, cetyl alcohol, glyceryl monostearate, lanolin, and stearic acid. Certain preferred water-soluble ointment bases are generally prepared from polyethylene glycols of varying molecular weight.

Creams, as also well known in the art, are viscous liquids or semisolid emulsions, typically either oil-in-water or water-in-oil. Cream bases are water-washable, and typically contain an aqueous phase, an oil phase, an emulsifier. The aqueous phase (e.g., water), usually, although not necessarily, exceeds the oil phase in volume, and generally contains a humectant. The oil phase is generally comprised of petrolatum and a fatty alcohol such as cetyl or stearyl alcohol. The emulsifier in a cream formulation is generally a nonionic, anionic, cationic, or amphoteric surfactant.

Lotions are preparations to be applied to the skin surface without substantial friction, and are typically liquid or semiliquid preparations in which the active agent is present in a water or alcohol base. Lotions may also be suspensions of solids, and may comprise a liquid oily emulsion of the oil-in-water type. In certain embodiments, lotions may be preferred for treating larger body areas, because of the ease of applying a more fluid composition. Lotions will typically contain suspending agents to produce better dispersions as well as compounds useful for localizing and holding the active agent in contact with the skin, e.g., methylcellulose, sodium carboxymethylcellulose, or the like.

Gels employed in the field of pharmaceutical formulation are semisolid, suspension-type systems. Single-phase gels contain organic macromolecules distributed substantially uniformly throughout the carrier liquid, which is typically aqueous, but also, preferably, contains an alcohol and, optionally, an oil. Preferred gelling agents, are crosslinked acrylic acid polymers such as the carbomer family of polymers, e.g., carboxypolyalkylenes that may be obtained commercially (e.g., Carbopol® and the like). Other exemplary hydrophilic polymers include polyethylene oxides, polyoxyethylene-polyoxypropylene copolymers, and polyvinylalcohol; cellulosic polymers such as hydroxypropyl cellulose, hydroxyethyl cellulose, hydroxypropyl methylcellulose, hydroxypropyl methylcellulose phthalate, and methyl cellulose; gums such as tragacanth and xanthan gum; sodium alginate; and gelatin. In order to prepare a uniform gel, dispersing agents such as alcohol or glycerin can be added, or the gelling agent can be dispersed by trituration, mechanical mixing, or stirring, or combinations thereof.

Pastes are semisolid dosage forms in which the active agent is suspended in a suitable base. Depending on the nature of the base, pastes may be divided between fatty pastes or those made from a single-phase aqueous gels. The base in a fatty paste is generally petrolatum, hydrophilic petrolatum, or the like. The pastes made from single-phase aqueous gels generally incorporate carboxymethylcellulose or the like as a base.

As noted above, topical formulations may also be prepared with liposomes, micelles, and microspheres. Liposomes are microscopic vesicles having a lipid wall comprising a lipid bilayer, and can be used as drug delivery systems herein as well. Generally, liposome formulations are preferred for poorly soluble or insoluble pharmaceutical agents. Liposomal preparations may include cationic (positively charged), anionic (negatively charged), and neutral preparations. Cationic liposomes are readily available and include, for example, N[1-2,3-dioleyloxy)propyl]-N,N,N-triethylammonium (DOTMA) liposomes are available under the tradename Lipofectin® (GIBCO BRL, Grand Island, N.Y.). Similarly, anionic and neutral liposomes are readily available as well, e.g., from Avanti Polar Lipids (Birmingham, Ala.), or can be easily prepared using readily available materials. Such materials include phosphatidyl choline, cholesterol, phosphatidyl ethanolamine, dioleoylphosphatidyl choline (DOPC), dioleoylphosphatidyl glycerol (DOPG), and dioleoylphosphatidyl ethanolamine (DOPE), among others. These materials can also be mixed with DOTMA in appropriate ratios. Methods for making liposomes using these materials are well known in the art.

Micelles are known in the art as comprised of surfactant molecules arranged so that their polar headgroups form an outer spherical shell, while their hydrophobic, hydrocarbon chains are oriented towards the center of the sphere, forming a core. Micelles form in an aqueous solution containing surfactant at a high enough concentration so that micelles naturally result. Surfactants useful for forming micelles include, but are not limited to, potassium laurate, sodium octane sulfonate, sodium decane sulfonate, sodium dodecane sulfonate, sodium lauryl sulfate, docusate sodium, decyltrimethylammonium bromide, dodecyltrimethylammonium bromide, tetradecyltrimethylammonium bromide, tetradecyltrimethylammonium chloride, dodecylammonium chloride, polyoxyl 8 dodecyl ether, polyoxyl 12 dodecyl ether, nonoxynol 10, and nonoxynol 30. Micelle formulations can be used in conjunction with the present disclosure either by incorporation into the reservoir of a topical or transdermal delivery system, or into a formulation to be applied to the body surface.

Microspheres, similarly, may be incorporated into the present topical formulations and drug delivery systems. Like liposomes and micelles, microspheres essentially encapsulate a drug or drug-containing formulation. Microspheres are generally, although not necessarily, formed from synthetic or naturally occurring biocompatible polymers, but may also be comprised of charged lipids such as phospholipids. Preparation of microspheres is well known in the art and described in the pertinent texts and literature.

The choice of a particular formulation carrier or vehicle will depend on the particular physical form and mode of delivery that the formulation is to achieve. Suitable topical vehicles and vehicle components for use with the formulations described herein (including, for example, the physical dose forms discussed above) are well known in the cosmetic and pharmaceutical arts, and include such vehicles (or vehicle components) and carriers as water; organic solvents such as alcohols (particularly lower alcohols readily capable of evaporating from the skin such as ethanol), glycols (such as propylene glycol, butylene glycol, and glycerin), aliphatic alcohols (such as lanolin); mixtures of water and organic solvents (such as water and alcohol), and mixtures of organic solvents such as alcohol and glycerin (optionally also with water); lipid-based materials such as fatty acids, acylglycerols (including oils, such as mineral oil, and fats of natural or synthetic origin), phosphoglycerides, sphingolipids and waxes; protein-based materials such as collagen and gelatin; silicone-based materials (both non-volatile and volatile) such as cyclomethicone, demethiconol and dimethicone copolyol (Dow Corning); hydrocarbon-based materials such as petrolatum and squalane; anionic, cationic and amphoteric surfactants and soaps; sustained-release vehicles such as microsponges and polymer matrices; stabilizing and suspending agents; emulsifying agents; and other vehicles and vehicle components that are suitable for administration to the skin, as well as mixtures of topical vehicle components as identified above or otherwise known to the art. In one particular embodiment, the carrier or vehicle comprises water. The vehicle may further include components adapted to improve the stability or effectiveness of the applied formulation, such as preservatives, antioxidants, skin penetration enhancers, sustained release materials, and the like. Examples of such vehicles and vehicle components are well known in the art and are described in such reference works as Martindale—The Extra Pharmacopoeia (Pharmaceutical Press, London 1993) and Remington's Pharmaceutical Sciences.

In certain embodiments, the formulation includes a solvent. Suitable solvents for use in the formulations of the present invention include, but are not limited to, water, ethanol, butylene glycol, propylene glycol, isopropyl alcohol, isoprene glycol, glycerin, Carbowax 200, Carbowax 400, Carbowax 600, and Carbowax 800. In addition, combinations or mixtures of these solvents may be used according to the present invention. In one particular embodiment, the solvent is water.

Depending on the particular physical dose form, an emulsifier may be included. Suitable emulsifiers for use in the formulations described herein include, but are not limited to, Incroquat Behenyl TMS (behentrimonium methosulfate, cetearyl alcohol), non-ionic emulsifiers like polyoxyethylene oleyl ether, PEG-40 stearate, ceteareth-12 (e.g., Eumulgin B-1 manufactured by Henkel), ceteareth-20 (e.g., Eumulgin B-2 manufactured by Henkel), ceteareth-30, Lanette O (manufactured by Henkel; ceteareth alcohol), glyceryl stearate (e.g., Cutina GMS manufactured by Henkel), PEG-100 stearate, Arlacel 165 (glyceryl stearate and PEG-100 stearate), steareth-2 and steareth-20, or combinations/mixtures thereof, as well as cationic emulsifiers like stearamidopropyl dimethylamine and behentrimonium methosulfate, or combinations/mixtures thereof. In addition, cationic emulsifiers may be combined or mixed with non-ionic emulsifiers.

Suitable viscosity adjusting agents (i.e., thickening and thinning agents) for the formulations described herein include, but are not limited to, protective colloids or non-ionic gums such as hydroxyethylcellulose (e.g., Cellosize HEC QP52,000-H, manufactured by Amerchol), xanthan gum, and sclerotium gum (Amigel 1.0), as well as magnesium aluminum silicate (Veegum Ultra), silica, microcrystalline wax, beeswax, paraffin, and cetyl palmitate. In addition, appropriate combinations or mixtures of these viscosity adjusters may be utilized.

Suitable surfactants for use in the formulations of the present invention include, but are not limited to, nonionic surfactants like Surfactant 190 (dimethicone copolyol), Polysorbate 20 (Tween 20), Polysorbate 40 (Tween 40), Polysorbate 60 (Tween 60), Polysorbate 80 (Tween 80), lauramide DEA, cocamide DEA, and cocamide MEA, amphoteric surfactants like oleyl betaine and cocamidopropyl betaine (Velvetex BK-35), and cationic surfactants like Phospholipid PTC (Cocamidopropyl phosphatidyl PG-dimonium chloride). Combinations of surfactants may also be employed.

The formulations may also included one or more preservatives. Suitable preservatives include, but are not limited to, anti-microbials such as Germaben II (manufactured by ICI; propylene glycol, diazolidinyl urea, methylparaben, and propylparaben), methylparaben, propylparaben, imidazolidinyl urea, benzyl alcohol, sorbic acid, benzoic acid, sodium benzoate, dichlorobenzyl alcohol, and formaldehyde, as well as physical stabilizers and anti-oxidants such as alpha-tocopherol (vitamin E), sodium ascorbate/ascorbic acid, ascorbyl palmitate and propyl gallate. In addition, combinations or mixtures of these preservatives may also be used.

Various additives, known to those skilled in the art, may also be included in the topical formulations. In certain embodiments, for example, it may be desirable to include one or more skin permeation enhancers in the formulation. Examples of suitable enhancers include, but are not limited to, ethers such as diethylene glycol monoethyl ether (available commercially as Transcutol®) and diethylene glycol monomethyl ether; surfactants such as sodium laurate, sodium lauryl sulfate, cetyltrimethylammonium bromide, benzalkonium chloride, Poloxamer (231, 182, 184), Tween (20, 40, 60, 80), and lecithin (U.S. Pat. No. 4,783,450); alcohols such as ethanol, propanol, octanol, benzyl alcohol, and the like; polyethylene glycol and esters thereof such as polyethylene glycol monolaurate (PEGML; see, e.g., U.S. Pat. No. 4,568,343); amides and other nitrogenous compounds such as urea, dimethylacetamide (DMA), dimethylformamide (DMF), 2-pyrrolidone, 1-methyl-2-pyrrolidone, ethanolamine, diethanolamine, and triethanolamine; terpenes; alkanones; and organic acids, particularly citric acid and succinic acid. Azone® and sulfoxides such as DMSO and C10 MSO may also be used.

Other enhancers are those lipophilic co-enhancers typically referred to as "plasticizing" enhancers, i.e., enhancers that have a molecular weight in the range of about 150 to 1000, and an aqueous solubility of less than about 1 wt. %. Lipophilic enhancers include fatty esters, fatty alcohols, and fatty ethers. Examples of specific fatty acid esters include methyl laurate, ethyl oleate, propylene glycol monolaurate, propylene glycerol dilaurate, glycerol monolaurate, glycerol monooleate, isopropyl n-decanoate, and octyldodecyl myristate. Fatty alcohols include, for example, stearyl alcohol and oleyl alcohol, while fatty ethers include compounds wherein a diol or triol, e.g., a C2-C4 alkane diol or triol, is substituted with one or two fatty ether substituents.

Additional permeation enhancers will be known to those of ordinary skill in the art of topical drug delivery, and/or are described in the pertinent texts and literature. See, e.g., Percutaneous Penetration Enhancers, eds. Smith et al. (CRC Press, 1995).

The formulations may also comprise one or more moisturizers. Suitable moisturizers for use in the formulations of the present disclosure include, but are not limited to, lactic acid and other hydroxy acids and their salts, glycerin, propylene glycol, butylene glycol, sodium PCA, Carbowax 200, Carbowax 400, and Carbowax 800. Suitable emollients for use in the formulations described herein include, but are not limited to, PPG-15 stearyl ether, lanolin alcohol, lanolin, lanolin derivatives, cholesterol, petrolatum, isostearyl neopentanoate, octyl stearate, mineral oil, isocetyl stearate, Ceraphyl 424 (myristyl myristate), octyl dodecanol, dimethicone (Dow Corning 200-100 cps), phenyl trimethicone (Dow Corning 556), Dow Corning 1401 (cyclomethicone and dimethiconol), and cyclomethicone (Dow Corning 344), and Miglyol 840 (manufactured by Huls; propylene glycol dicaprylate/dicaprate). In addition, appropriate combinations and mixtures of any of these moisturizing agents and emollients may be used in accordance with the present invention.

Suitable fragrances and colors, such as FD&C Red No. 40 and FD&C Yellow No. 5, may also be used in the formulations. Other examples of fragrances and colors suitable for use in topical products are known in the art.

Other suitable additional and adjunct ingredients which may be included in the formulations of the present invention include, but are not limited to, abrasives, absorbents, anti-caking agents, anti-foaming agents, anti-static agents, astringents (e.g., witch hazel, alcohol, and herbal extracts such as chamomile extract), binders/excipients, buffering agents, chelating agents (e.g., Versene EDTA), film forming agents, conditioning agents, opacifying agents, pH adjusters (e.g., citric acid and sodium hydroxide), and protectants. Examples of each of these ingredients, as well as examples of other suitable ingredients in topical product formulations, may be found in publications by The Cosmetic, Toiletry, and Fragrance Association (CTFA). See, e.g., CTFA Cosmetic Ingredient Handbook, 2nd edition, eds. John A. Wenninger and G. N. McEwen, Jr. (CTFA, 1992).

The formulations may also contain irritation-mitigating additives to minimize or eliminate the possibility of skin irritation or skin damage resulting from the pharmacologically active base or other components of the composition. Suitable irritation-mitigating additives include, for example: alpha-tocopherol; monoamine oxidase inhibitors, particularly phenyl alcohols such as 2-phenyl-1-ethanol; glycerin; salicylic acids and salicylates; ascorbic acids and ascorbates; ionophores such as monensin; amphiphilic amines; ammonium chloride; N acetyl cysteine; cis-urocanic acid; capsaicin; and chloroquine. The irritant-mitigating additive, if present, may be incorporated into the present formulations at a concentration effective to mitigate irritation or skin damage.

The compositions and formulations described herein can be administered in accordance with a number of topical delivery routes and/or mechanisms. The method of delivery of the compositions may vary, but generally involves application of a formulation comprising hydroxytyrosol to an area of body surface affected with a wound, or the area surrounding such wound (i.e., the peri wound). For example, in one embodiment gels may be preferred for areas in which there is a partial or total loss of skin layers (Stage II, III or IV wounds) and ointments will be prepared for areas in which the skin appears to be intact to the unaided eye. Typical modes of delivery include application using the fingers; application using a physical applicator such as a cloth, tissue, swab, stick or brush (as achieved for example by soaking the applicator with the formulation just prior to application, or by applying or adhering a prepared applicator already containing the formulation—such as a treated or premoistened bandage, wipe, washcloth or stick—to the skin); spraying (including mist, aerosol or foam spraying); dropper application (as for example with ear drops); sprinkling (as with a suitable powder form of the formulation); and soaking. A gel, cream, ointment, or lotion, for example, may be spread on the affected surface and optionally gently rubbed in. A solution may be applied in like manner, but more typically will be applied with a dropper, swab, or the like, and carefully applied to the affected areas. Solutions may also be sprayed onto a surface using a spray applicator; being mixed with fibrin glue and applied (e.g., sprayed) onto a surface. In some embodiments, a composition of the present invention may be impregnated into absorptive materials, such as dressings, bandages, patches, and gauze, or coated onto the surface of solid phase materials, and placed on an affected area, with or without the use of gentle pressure and/or an adhesive material to secure the material to the area.

Other types and configurations of topically applied drug delivery systems may also be used in conjunction with the present invention, as will be appreciated by those skilled in the art of transdermal drug delivery. See, for example, Ghosh, Transdermal and Topical Drug Delivery Systems (Interpharm Press, 1997), particularly Chapters 2 and 8.

The dose regimen will depend on a number of factors that may readily be determined, such as severity of the affected region and responsiveness of the condition to be treated, but will normally be one or more doses per day, with a course of treatment lasting from several days to several months, or until a cure is effected or a diminution of disease state is achieved. One of ordinary skill may readily determine optimum dosages, dosing methodologies, and repetition rates. In general, it is contemplated that the formulation will be applied one to four times daily. With a skin patch, bandage, or dressing, the device is generally maintained in place on the body surface throughout a drug delivery period, typically in the range of 8 to 72 hours, and replaced as necessary.

The method of promoting cell health of the cells of a mammal is useful for, among other things, the treatment or prevention of skin ailments. Treatment of lymphedema-induced pruritis and of ichthyosis with an effective amount of the composition of the present invention is shown to treat or palliate the skin manifestations occurring in these disorders. Topical formulations were effective upon following the treatment regimen.

Without seeking to limit the invention or to be bound by any particular theory, it is believed that promoting or maintaining cell health of the cells of a mammal by administering a therapeutically effective amount of a composition of the present invention may act through one or more of the following mechanisms: a) treating or preventing oncosis or extended quiescence of the cells; b) maintaining or increasing the amount of adenosine triphosphate (ATP) in the extracellular spaces within a mammal; c) repairing the cell membranes within a mammal; d) restoring the normal osmotic balance across the cell membranes or stopping the flow of sodium ions in the cells; e) activating quiescent cells that have not moved normally through the cell cycle; f) protecting against free radical damage to the cell, its organelles and the extracellular spaces; and g) protecting against cellular necrosis during the pre-lethal stages.

In the present invention, an "effective amount" or "therapeutically effective amount" of a compound or of a composition of the present invention is that amount of such compound and/or composition that is sufficient to effect beneficial or desired results as described herein. In terms of treatment of a mammal, e.g., a human patient, an "effective amount" is an amount sufficient to treat, reduce, manage, palliate, ameliorate, or stabilize a condition, such as a non-congenital oncosis or extended quiescence of the cells of a mammal, or both, as compared to the absence of the compound or composition.

Having described the invention in detail, it will be apparent that modifications and variations are possible without departing the scope of the invention defined in the appended claims.

What is claimed is:

1. A process for treating a skin wound characterized by a partial or total loss of skin, the wound being surrounded by a peri-wound region, the process comprising topically applying a first composition to the peri-wound region, the first composition comprising hydroxytyrosol, N-acetyl cysteine and at least one member selected from the group consisting of glycine, L-taurine, L-proline, methylsulfonylmethane, niacinamide, pyridoxine and combinations thereof, wherein said hydroxytyrosol is present in a concentration from 5 µM to 250 µM hydroxytyrosol, and wherein the weight ratio of N-acetyl cysteine to hydroxytyrosol is between 1:1 and 50:1.

2. The process of claim 1 wherein the concentration of hydroxytyrosol in the first composition is from 5 µM to less than 225 µM.

3. The process of claim 1 wherein the concentration of hydroxytyrosol is from 10 to 200 µM.

4. The process of claim 1 wherein a second composition is applied to the wound region, the second composition containing hydroxytyrosol in a concentration that is less than the concentration of hydroxytyrosol in the first composition and less than 15 µM.

5. A process for treating a skin wound characterized by a partial or total loss of skin, the wound being surrounded by a peri-wound region, the process comprising topically applying a composition to the open wound region, the composition comprising hydroxytyrosol, N-acetyl cysteine and at least one member selected from the group consisting of glycine, L-taurine, L-proline, methylsulfonylmethane, niacinamide, pyridoxine and combinations thereof, wherein said hydroxytyrosol is present in a concentration of less than 15 µM, and wherein the weight ratio of N-acetyl cysteine to hydroxytyrosol is between 1:1 and 50:1.

6. The process of claim 5 wherein the hydroxytyrosol concentration is less than 12 µM.

7. A process for inhibiting excessive transepidermal water loss through the stratum corneum, the process comprising topically applying an aqueous composition to the stratum corneum, the aqueous composition comprising hydroxytyrosol, N-acetyl cysteine and at least one member selected from the group consisting of glycine, L-taurine, L-proline, methylsulfonylmethane, niacinamide, pyridoxine and combinations thereof, wherein said hydroxytyrosol is present in a concentration of 5 µM to 250 µM, and wherein the weight ratio of N-acetyl cysteine to hydroxytyrosol is between 1:1 and 50:1.

8. The process of claim 7 wherein the hydroxytyrosol concentration is less than 10 µM.

9. The process of claim 7 wherein the concentration of hydroxytyrosol in the composition is 7 to 225 µM.

10. The process of claim 7 wherein the concentration of hydroxytyrosol in the composition is 10 to 200 µM.

11. A process for treating skin that is distressed or wounded as a result of a disease or other metabolic condition but appearing intact to the unaided eye, the process comprising topically applying an aqueous composition to the skin, the aqueous composition comprising hydroxytyrosol, N-acetyl cysteine and at least one member selected from the group consisting of glycine, L-taurine, L-proline, methylsulfonylmethane, niacinamide, pyridoxine and combinations thereof, wherein said hydroxytyrosol is present in a concentration of 5 µM to 250 µM and wherein the weight ratio of N-acetyl cysteine to hydroxytyrosol is between 1:1 and 50:1.

12. The process of claim 11 wherein the concentration of hydroxytyrosol in the composition is less than 225 µM.

13. The process of claim 11 wherein the concentration of hydroxytyrosol is between 15 and 225 µM.

14. The process of claim 11 wherein the concentration of hydroxytyrosol is between 15 and 200 µM.

15. The process of claim 11 wherein the concentration of hydroxytyrosol is between 12 and 200 µM.

16. The process of claim 11 wherein the concentration of hydroxytyrosol is less than 15 μM.

17. The process of claim 11 wherein the concentration of hydroxytyrosol is less than 12 μM.

18. The process of claim 11 wherein the concentration of hydroxytyrosol is less than 10 μM.

19. An aqueous composition for wound care, the composition comprising hydroxytyrosol, N-acetyl cysteine and at least one member selected from the group consisting of glycine, L-taurine, L-proline, methylsulfonylmethane, niacinamide, pyridoxine and combinations thereof, wherein said hydroxytyrosol is present in a concentration of 1 μM to 250 μM, and wherein the weight ratio of N-acetyl cysteine to hydroxytyrosol is between 1:1 and 50:1.

20. The composition of claim 19 wherein the concentration of hydroxytyrosol in the composition is less than 225 μM.

21. The composition of claim 19 wherein the concentration of hydroxytyrosol is between 15 and 225 μM.

22. The composition of claim 19 wherein the concentration of hydroxytyrosol is between 15 and 200 μM.

23. The composition of claim 19 wherein the concentration of hydroxytyrosol is between 12 and 200 μM.

24. The composition of claim 19 wherein the concentration of hydroxytyrosol is less than 15 μM.

25. The composition of claim 19 wherein the concentration of hydroxytyrosol is less than 12 μM.

26. The composition of claim 19 wherein the concentration of hydroxytyrosol is less than 10 μM.

27. The composition of claim 19 wherein the weight ratio of N-acetyl cysteine to hydroxytyrosol is between 10:1 and 30:1.

28. The composition of claim 27 wherein the weight ratio of N-acetyl cysteine to hydroxytyrosol is between 20:1 and 25:1.

29. The composition of claim 19 wherein the weight ratio of glycine to hydroxytyrosol is between 1:1 and 50:1, respectively.

30. The composition of claim 19 wherein the weight ratio of L-taurine to hydroxytyrosol is between 1:1 and 50:1, respectively.

31. The composition of claim 19 wherein the weight ratio of L-proline to hydroxytyrosol is between 1:1 and 20:1, respectively.

32. The composition of claim 19 wherein the weight ratio of methylsulfonylmethane to hydroxytyrosol is between 1:1 and 30:1, respectively.

33. The composition of claim 19 wherein the weight ratio of niacinamide to hydroxytyrosol is between 1:1 and 10:1, respectively.

34. The composition of claim 19 wherein the weight ratio of pyridoxine to hydroxytyrosol is between 1:1 and 10:1, respectively.

35. The composition of claim 19 wherein the hydroxytyrosol is present in the composition as a hydroxytyrosol salt.

36. The composition of claim 19 wherein the composition is in the form of a cream, lotion, solution, suspension, emulsion, gel, ointment, or paste.

37. A process for treating a skin wound characterized by a partial or total loss of skin, the wound being surrounded by a peri-wound region, the process comprising topically applying a first composition to the peri-wound region, the first composition comprising from 5 μM to 250 μM hydroxytyrosol and N-acetyl cysteine, wherein the weight ratio of N-acetyl cysteine to hydroxytyrosol is between 1:1 and 50:1, and topically applying a second composition to the wound region, the second composition containing hydroxytyrosol in a concentration that is less than the concentration of hydroxytyrosol in the first composition and less than 15 μM, wherein the weight ratio of N-acetyl cysteine to hydroxytyrosol in the second composition is between 1:1 and 50:1.

38. The process of claim 37 wherein the concentration of hydroxytyrosol in the first composition is less than 225 μM.

39. The process of claim 37 wherein the concentration of hydroxytyrosol in the first composition is from 10 to 200 μM.

* * * * *